United States Patent
Flower et al.

(10) Patent No.: US 6,810,161 B2
(45) Date of Patent: Oct. 26, 2004

(54) INTEGRATING CAVITY FOR OPTICAL MEASUREMENTS

(75) Inventors: John T. Flower, Longmont, CO (US); Christopher S. Wood, Boulder, CO (US); Shirley Thorkelson, Belgrade, MT (US)

(73) Assignee: ILX Lightwave Corporation, Bozeman, MT (US)

(*) Notice: Subject to any disclaimer, the term of this patent is extended or adjusted under 35 U.S.C. 154(b) by 0 days.

(21) Appl. No.: 10/324,519

(22) Filed: Dec. 19, 2002

(65) Prior Publication Data

US 2003/0152311 A1 Aug. 14, 2003

Related U.S. Application Data

(60) Provisional application No. 60/344,144, filed on Dec. 27, 2001.

(51) Int. Cl.[7] .................................................. G02B 6/26
(52) U.S. Cl. .............................. 385/15; 385/88; 385/92
(58) Field of Search ............................. 385/33, 88, 92, 385/15; 356/236, 319, 323, 326; 250/228; 248/664, 288.31

(56) References Cited

U.S. PATENT DOCUMENTS

| | | | | |
|---|---|---|---|---|
| 3,432,243 A | * | 3/1969 | Hardesty ..................... | 356/405 |
| 4,120,582 A | * | 10/1978 | De Vries et al. ............. | 356/73 |
| 4,310,249 A | * | 1/1982 | Kramer ....................... | 356/414 |
| 4,645,922 A | * | 2/1987 | Welbourn et al. ........... | 250/226 |
| 4,868,383 A | * | 9/1989 | Kurtz et al. ................. | 250/228 |
| 6,040,904 A | * | 3/2000 | Fallet et al. ................. | 356/236 |
| 6,369,883 B1 | * | 4/2002 | Clark ......................... | 356/73.1 |

OTHER PUBLICATIONS

"Spectralon Reflectance Material for Component Fabrication", Labsphere–Spectralon Reflectance Material, http//www.labsphere.com/products/products asp? CID=37&PID=1 125, Mar. 25, 2003, pp. 1–2.
"SRM–99L Laser Grade Spectralon Material", Labsphere–SRM Laser Grade. http //www.labsphere com/products/products.asp? CID=37&PID=369, Mar. 25, 2003, 1 page.
"SRM–995 Space Grade Spectralon Material", Labspere–SRM Space Grade. http://www.labsphere com/products/products.asp? CID=37&PID=370, Mar. 25, 2003, 1 page.
"SRM–99L OpticalGrade Spectralon Material", Labsphere–SRM Optical Grade, http //www labsphere com/products/products.asp? CID=37&PID=368, Mar. 25, 2003, pp. 1–2.

* cited by examiner

*Primary Examiner*—Michael G. Lee
*Assistant Examiner*—Kumiko C. Koyama
(74) *Attorney, Agent, or Firm*—Lathrop & Gage, L.C.

(57) ABSTRACT

An integrating optical system for measuring optical radiation. The system has a first sphere (forming a "primary" integrating cavity) and a second sphere (forming a "secondary" integrating cavity). An optical fiber interfaces to an input aperture of the first sphere so that light from the fiber enters the first sphere. A detector interfaces with the second sphere such that light from the first sphere couples to the detector by scattering within the first and second spheres and without a direct line of sight between the detector and the input aperture. The secondary integrating cavity has a smaller volume than the primary integrating cavity. The secondary integrating cavity is made smaller so as to decrease losses incurred by light scattering transmission through the first and second spheres. The detector is preferably configured so that it does not receive "specular" radiation (i.e., radiation from a single reflection) from the walls of the primary cavity.

12 Claims, 3 Drawing Sheets

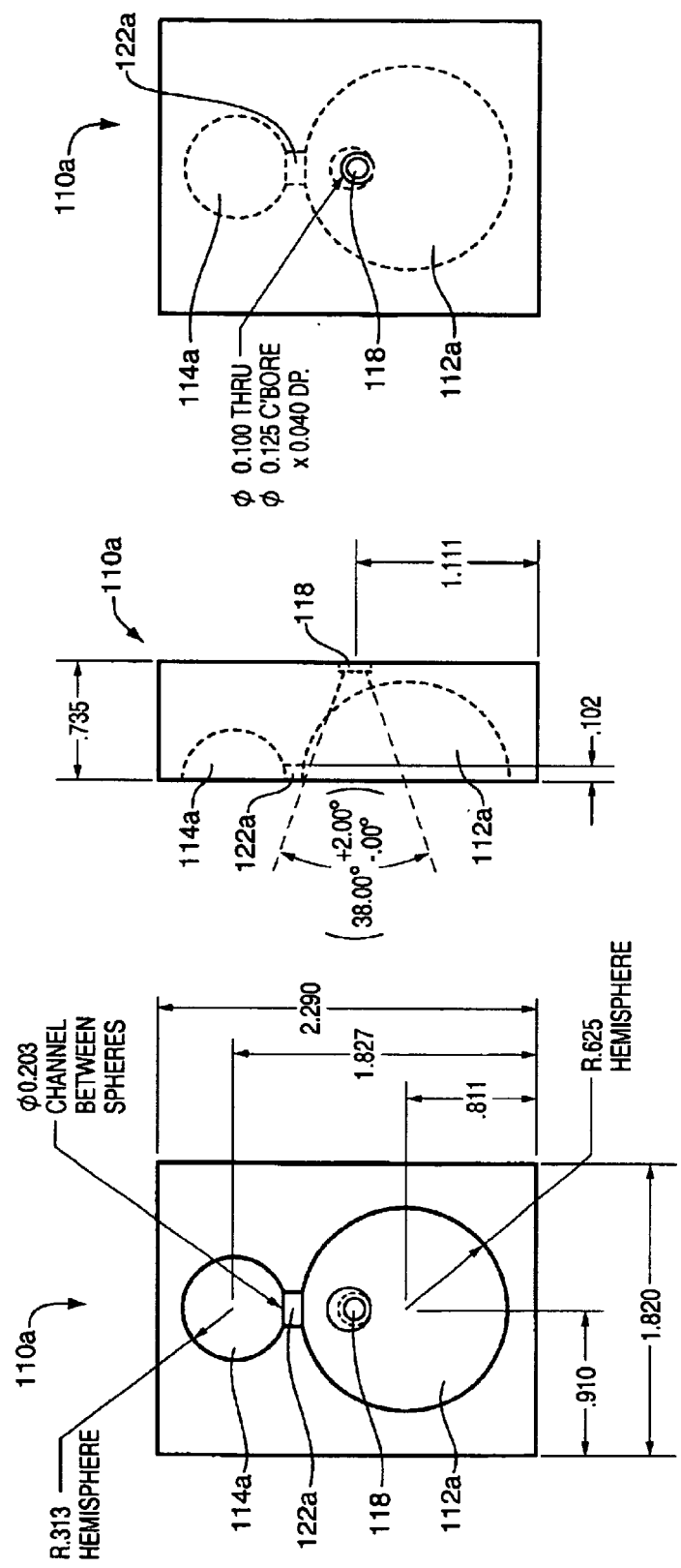

INTEGRATING CAVITY FOR OPTICAL MEASUREMENTS

RELATED APPLICATIONS

This application claims priority to U.S. provisional application Ser. No. 60/344,144, filed Dec. 27, 2001, entitled "INTEGRATING CAVITY FOR OPTICAL MEASUREMENTS" and which is incorporated herein by reference.

BACKGROUND OF THE INVENTION

The use of integrating cavities, or "integrating spheres," to diffuse electromagnetic radiation is known in the prior art. These cavities are for example used in spectrophotometers and other optical instrumentation to diffuse source intensity nonuniformities and various polarization states. Integrating cavities are sometimes used to approximate a Lambertian radiator or as an integrator of incident radiant flux.

As the optical sensitivities of modem detectors and optical fibers increase, the qualifications needed in integrating cavities also increase. By way of example, when the output of a polarization dependent optical component (e.g., an optical fiber) is measured by a detector through an integrating cavity, it is desirable to minimize any influence the cavity may have on measured polarization dependencies.

A further complication of the prior art is that optical cavities are often used by manually coupling one component, e.g., an optical fiber, to the cavity. The resulting signal through the cavity is quite dependent on the physical placement of the component with the cavity, making it quite difficult to achieve repeated test measurements.

There is therefore the need to provide an improved integrating cavity for optical measurement. The invention overcomes the problems in the prior art by providing, in one feature, an integrating optical cavity system that reduces polarization and input emission variations. Other features of the invention will be apparent in the description that follows.

SUMMARY OF THE INVENTION

In one aspect, the invention provides an integrating optical system for measuring optical radiation. The system has a first sphere (forming a "primary" integrating cavity) and a second sphere (forming a "secondary" integrating cavity). An optical fiber interfaces to an input aperture of the first sphere so that light from the fiber enters the first sphere. A detector interfaces with the second sphere such that light from the first sphere couples to the detector by scattering within the first and second spheres and without a direct line of sight between the detector and the input aperture. The secondary integrating cavity has a smaller volume than the primary integrating cavity.

In the preferred aspect of the invention, each of the inner walls of the spheres is made from SPECTRALON® material from Labsphere. The secondary integrating cavity is made smaller so as to decrease losses incurred by light scattering transmission through the first and second spheres. The detector is preferably configured so that it does not receive "specular" radiation (i.e., radiation from a single reflection) from the walls of the primary cavity. Those skilled in the art should appreciate that the first and second integrating cavities may take different shapes other than spheres without departing from the scope of the invention.

In one aspect, the system utilizes an off center entrance cone as an input port for the optical fiber. The detector, likewise, may also be off-center as a matter of design choice.

The invention provides certain advantages. First, the detector is physically decoupled from the first sphere and is therefore not in direct line of sight to the input aperture. This configuration reduces effects of polarization orientation and of input patterns due to rotation about the longitudinal dimension of the input optical fiber; accordingly, the configuration provides for enhanced repeatability in production test environments. More particularly, the lack of polarization response allows measurement of polarization dependent loss in fiber optic components by varying the input state of polarization. A detector in the form of a low polarization response meter provides for monitoring change in output associated with the input polarization of the component under test,, and not for the test equipment polarization sensitivities. Moreover, in the preferred aspect, the invention permits full capture of diverging radiation from the optical fiber. Finally, the invention provides for high repeatability in test measurements.

In another aspect, the invention provides for wavelength detection. The system of this aspect includes a colored filter in front of the detector. A detector measurement is made to generate detector current output. Other filters and detectors may be used in sequence (or concurrently, as described below) to generate a ratio of detector currents with wavelength.

In still another aspect, the invention provides a test system that has broad and flat spectral response characteristics, e.g., utilizing InGaAs and Si detectors.

In yet another aspect, a second detector couples with the second sphere so as to provide further reduction in polarization response. By way of example, the responses from the two detectors may be averaged together; the detectors may also be mounted ninety degrees from one another. Additional detectors may be coupled with the second sphere, and in different orientations, in accord with the invention.

In one aspect, the first sphere has a cone shaped cut-out formed with the input aperture, to accommodate the numerical aperture diverging light of the optical fiber.

BRIEF DESCRIPTION OF THE DRAWINGS

A more complete understanding of the invention may be obtained by reference to the drawings, in which:

FIG. 2a, FIG. 2b, and FIG. 2c show front, side and rear elevation views, respectively, of a front subassembly of one integrating optical system.

DETAILED DESCRIPTION OF THE DRAWINGS

Figure 1:
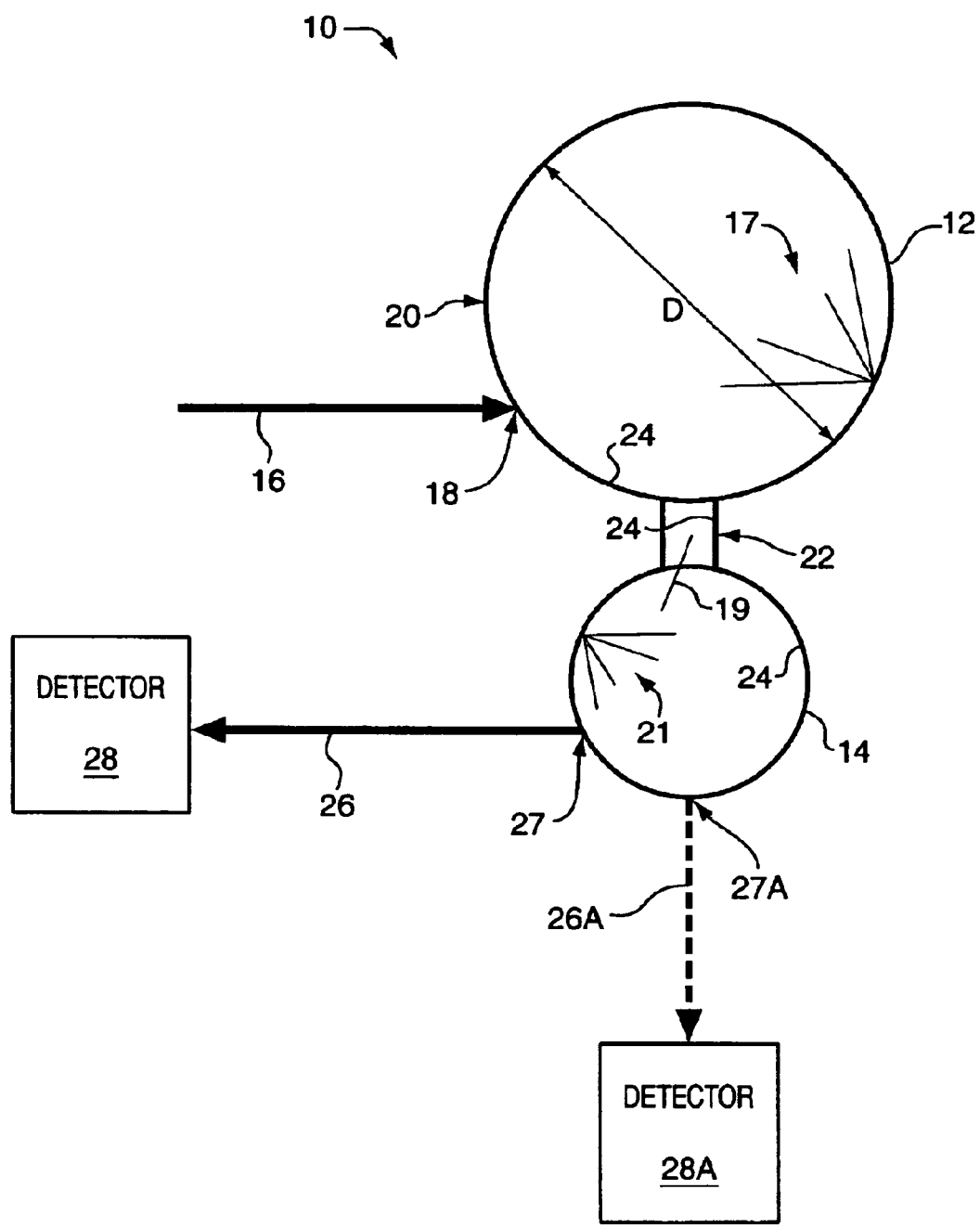
FIG. 1 shows one integrating optical system of the invention.

FIG. 1 shows an optical integrating system 10 of the invention. System 10 has a primary integrating sphere 12 and a secondary integrating sphere 14. Input optical energy 16 couples with sphere 12 in an input aperture location 18 that is "off center" from sphere center 20. Energy 16 is typically carried to sphere 12 via an optical fiber that injects energy to sphere 12 at an end-face (not shown) that is relatively small in comparison to sphere diameter D. Energy 16 scatters within system 10 as energy 17.

Optical energy 19 derives from energy 17 and couples between sphere 12 and sphere 14 via light conduit 22. Preferably, all inner surfaces 24 of system 10 are made with a white diffusing material such as SPECTRALON®.

Energy 19 scatters within sphere 14 as energy 21 and exits system 10 as output optical energy 26. A detector 28 may be used to measure energy 26 via an output aperture 27. Those skilled in the art should appreciate that detector 28 may couple directly with sphere 14 to detect energy 21. A second detector 28A may similarly detect energy 26A from a second aperture 27A as a matter of design choice. For example, detectors 28, 28A may be used synergistically to better measure polarization response. Other detectors (not shown) may further couple with sphere 14 as a matter of design choice.

FIG. 2a, FIG. 2b, and FIG. 2c show front, side and rear elevation views, respectively, of a front subassembly 110a of an integrating optical system. A hemisphere of a primary integrating cavity 112a, a hemisphere of a secondary integrating cavity 114a, an input aperture 118, and a light conduit 122a are shown. All dimensions are in inches.

Figure 3C:
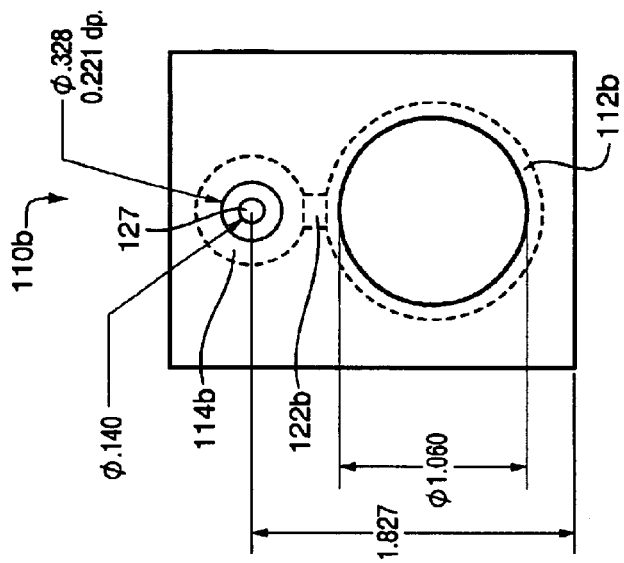
FIG. 3a, FIG. 3b, and FIG. 3c show front, side and rear elevation views, respectively, of a rear subassembly of the integrating optical system of FIGS. 2a, 2b and 2c.
Figure 3B:
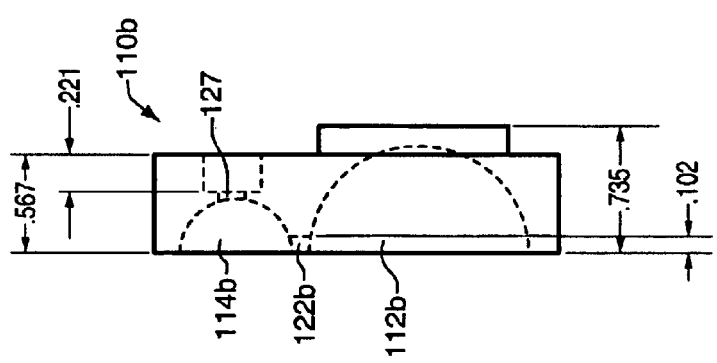
Figure 3A:
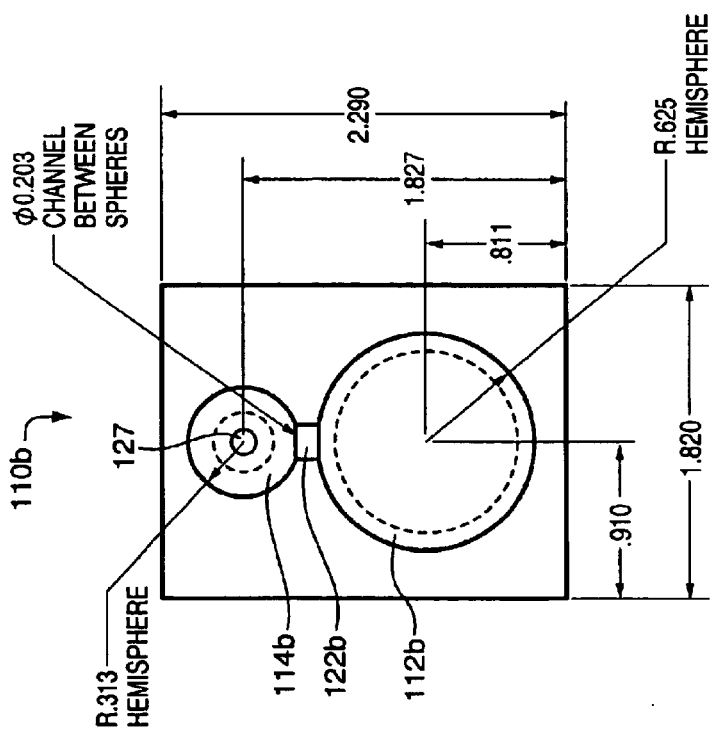

FIG. 3a, FIG. 3b, and FIG. 3c show front, side and rear elevation views. respectively, of a rear subassembly 110b of the integrating optical system of FIGS. 2a, 2b and 2c. A hemisphere of a primary integrating cavity 112b, a hemisphere of a secondary integrating cavity 114b. an output aperture 127. and a light conduit 122b are shown. All dimensions are in inches.

In view of the foregoing, what is claimed is:

1. An integrating optical system for measuring optical radiation, comprising:

a first sphere forming a primary integrating cavity and a second sphere forming a secondary integrating cavity, the second sphere having a volume smaller than the first sphere, the optical radiation passing unobstructed through a passageway between the first and second spheres;

an optical fiber interfacing to an input aperture of the first sphere so that the optical radiation from the fiber enters the first sphere; and a first detector interfacing with the second sphere such that the optical radiation from the first sphere couples to the detector by scattering within the first and second spheres, without a direct line of sight between the detector and the input aperture.

2. The system of claim 1, the first sphere forming an input cone with the input aperture to accommodate diverging radiation from the optical fiber.

3. The system of claim 1, the input aperture being off-center from an axial center of the first sphere.

4. The system of claim 1, the first detector interfacing with an output of the second sphere.

5. The system of claim 4, the output being off-center from an axial center of the second sphere.

6. The system of claim 1, further comprising an optical filter to filter radiation to the first detector, for wavelength detection.

7. The system of claim 1, the first detector comprising one of Si and InGaAs.

8. The system of claim 1, further comprising a second detector coupled with the second sphere.

9. The system of claim 8, the second detector being arranged about 90 degrees from the first detector, wherein averaging of signals from the first and second detectors provides improved polarization response.

10. The system of claim 1, wherein inner surfaces of the first sphere, the second sphere, and a conduit between the first and second spheres comprise white diffusing material.

11. The system of claim 1, wherein the input aperture is adapted to aim the optical radiation from the optical fiber away from the center of the first sphere.

12. The system of claim 1, further comprising a conduit between the first and second spheres, an interior of the conduit forming the passageway.

* * * * *